US010653314B2

(12) United States Patent
Pascal et al.

(10) Patent No.: US 10,653,314 B2
(45) Date of Patent: May 19, 2020

(54) METHODS AND SYSTEMS FOR ALIGNMENT OF OPHTHALMIC IMAGING DEVICES

(71) Applicant: Notal Vision Ltd., Tel Aviv (IL)

(72) Inventors: Amit Pascal, Haifa (IL); Omer Rafaeli, Udim (IL); Yair Alster, Tel Aviv (IL); Gidon Goren-Gratzyani, Givatayim (IL)

(73) Assignee: NOTAL VISION LTD., Tel-Aviv (IL)

( * ) Notice: Subject to any disclaimer, the term of this patent is extended or adjusted under 35 U.S.C. 154(b) by 0 days.

(21) Appl. No.: 16/425,362

(22) Filed: May 29, 2019

(65) Prior Publication Data

US 2019/0274545 A1    Sep. 12, 2019

Related U.S. Application Data

(63) Continuation of application No. PCT/IL2018/051172, filed on Nov. 4, 2018.
(Continued)

(51) Int. Cl.
*A61B 3/15*    (2006.01)
*A61B 3/113*    (2006.01)
(Continued)

(52) U.S. Cl.
CPC ............ *A61B 3/154* (2013.01); *A61B 3/0041* (2013.01); *A61B 3/0091* (2013.01); *A61B 3/024* (2013.01);
(Continued)

(58) Field of Classification Search
CPC ....... A61B 3/154; A61B 3/102; A61B 3/0041; A61B 3/113
See application file for complete search history.

(56) References Cited

U.S. PATENT DOCUMENTS 5,094,521 A    3/1992 Jolson et al.
5,838,424 A    11/1998 Wawro et al.
(Continued)

FOREIGN PATENT DOCUMENTS

WO    2016004385    1/2016

OTHER PUBLICATIONS

Chakravarthy et al., "Automated Identification of Lesion Activity in Neovascular Age-Related Macular Degeneration", Opthalmology, vol. 123, No. 8, Aug. 2016, pp. 1731-1736.
(Continued)

*Primary Examiner* — Jack Dinh
(74) *Attorney, Agent, or Firm* — Kilpatrick Townsend & Stockton LLP

(57) ABSTRACT

Ophthalmic imaging systems and related methods provide pseudo feedback to aid a user in aligning the user's eye with an optical axis of the imaging system. An ophthalmic imaging system includes an ophthalmic imaging device having an optical axis, a display device, an eye camera, and a control unit. The display device displays a fixation target viewable by the user. The eye camera images the eye to generate eye image data. The control unit processes the eye image data to determine a position of the eye relative to the optical axis, processes the position of the eye relative to the optical axis to generate a pseudo position of the eye relative to the optical axis, and causes the display device to display an indication that provides feedback to the user that the eye is located at the pseudo position of the eye relative to the optical axis.

24 Claims, 6 Drawing Sheets

Related U.S. Application Data

(60) Provisional application No. 62/582,779, filed on Nov. 7, 2017.

(51) Int. Cl.
  *A61B 3/00* (2006.01)
  *A61B 3/10* (2006.01)
  *A61B 3/08* (2006.01)
  *A61B 3/024* (2006.01)
  *A61B 3/11* (2006.01)

(52) U.S. Cl.
  CPC ............... *A61B 3/08* (2013.01); *A61B 3/102* (2013.01); *A61B 3/11* (2013.01); *A61B 3/113* (2013.01); *A61B 3/152* (2013.01)

(56) References Cited

U.S. PATENT DOCUMENTS

| | | | |
|---|---|---|---|
| 6,149,275 | A | 11/2000 | O'Shea |
| 6,980,363 | B1 | 12/2005 | Takagi et al. |
| 7,270,413 | B2 | 9/2007 | Hirohara et al. |
| 8,348,429 | B2 | 1/2013 | Walsh et al. |
| 8,384,908 | B2 | 2/2013 | Sugita et al. |
| 8,398,236 | B2 | 3/2013 | Juhasz et al. |
| 8,500,725 | B2 | 8/2013 | Raksi |
| 8,534,837 | B2 | 9/2013 | Sayeram et al. |
| 8,668,336 | B2 | 3/2014 | Buckland et al. |
| 8,842,287 | B2 | 9/2014 | Yazdanfar et al. |
| 9,144,379 | B1 | 9/2015 | Sims |
| 9,186,057 | B2 | 11/2015 | Borycki et al. |
| 9,192,295 | B1 | 11/2015 | Hathaway et al. |
| 9,420,947 | B2 | 8/2016 | Wei et al. |
| 9,538,916 | B2 | 1/2017 | Muto |
| 2003/0063386 | A1 | 4/2003 | Slawson et al. |
| 2008/0259274 | A1 | 10/2008 | Chinnock |
| 2009/0180074 | A1 | 7/2009 | Benyamini et al. |
| 2009/0268020 | A1 | 10/2009 | Buckland et al. |
| 2013/0033593 | A1 | 2/2013 | Chinnock et al. |
| 2013/0162948 | A1 | 6/2013 | Yazdanfar et al. |
| 2013/0235344 | A1 | 9/2013 | Buckland et al. |
| 2014/0002792 | A1 | 1/2014 | Filar |
| 2014/0009741 | A1 | 1/2014 | Levien et al. |
| 2014/0125952 | A1 | 5/2014 | Buckland et al. |
| 2014/0132924 | A1 | 5/2014 | Sagano et al. |
| 2014/0240674 | A1 | 8/2014 | Wei et al. |
| 2014/0340642 | A1 | 11/2014 | You et al. |
| 2015/0292860 | A1 | 10/2015 | Podoleanu et al. |
| 2015/0294147 | A1 | 10/2015 | Wisweh |
| 2015/0305618 | A1 | 10/2015 | Buckland et al. |
| 2015/0313467 | A1 | 11/2015 | Sakai et al. |
| 2016/0026847 | A1 | 1/2016 | Vugdelija et al. |
| 2016/0135681 | A1 | 5/2016 | Wakil et al. |
| 2016/0143529 | A1 | 5/2016 | Miyashita et al. |
| 2016/0183788 | A1 | 6/2016 | Abramoff et al. |
| 2017/0042422 | A1 | 2/2017 | Sakai et al. |
| 2017/0071466 | A1 | 3/2017 | Kowal et al. |
| 2017/0172407 | A1 | 6/2017 | Kowal et al. |
| 2017/0215725 | A1 | 8/2017 | Ishiai |
| 2017/0224208 | A1 | 8/2017 | Bublitz et al. |
| 2017/0227350 | A1 | 8/2017 | Sarunic et al. |
| 2017/0251920 | A1 | 9/2017 | Tokuda et al. |
| 2019/0090735 | A1 | 3/2019 | Fujii et al. |
| 2019/0254514 | A1 | 8/2019 | Westphal et al. |

OTHER PUBLICATIONS

PCT/IL2018/051172, "International Search Report and Written Opinion", dated Feb. 27, 2019, 12 pages.
PCT/IL2018/051174, "International Search Report and Written Opinion", dated Feb. 26, 2019, 8 pages.
U.S. Appl. No. 16/404,311, filed May 6, 2019.
U.S. Appl. No. 16/424,246, filed May 28, 2019.
U.S. Appl. No. 16/439,587, filed Jun. 12, 2019.
U.S. Appl. No. 16/404,311, "First Action Interview Pilot Program Pre-Interview Communication", Aug. 15, 2019, 4 pages.
U.S. Appl. No. 16/424,246, "First Action Interview Pilot Program Pre-Interview Communication", Jul. 31, 2019, 4 pages.
U.S. Appl. No. 16/439,587, "First Action Interview Pilot Program Pre-Interview Communication", Aug. 30, 2019, 5 pages.
U.S. Appl. No. 16/439,587, "Non-Final Office Action", dated Aug. 12, 2019, 14 pages.
U.S. Appl. No. 16/401,311 dated Feb. 28, 2020, 17 pages.

METHODS AND SYSTEMS FOR ALIGNMENT OF OPHTHALMIC IMAGING DEVICES

CROSS-REFERENCES TO RELATED APPLICATIONS

The present application is a Continuation of International Application No. PCT/IL2018/051172, filed Nov. 4, 2018, which claims the benefit of U.S. Provisional Application Ser. No. 62/582,779, filed on Nov. 7, 2017, the entire contents of which are hereby incorporated by reference in their entirety for all purposes.

BACKGROUND

Macular degeneration is the leading cause of vision loss in the United States of America. In macular degeneration, the central portion of the retina (a.k.a., the macula) deteriorates. When healthy, the macula collects and sends highly detailed images to the brain via the optic nerve. In early stages, macular degeneration typically does not significantly affect vision. If macular degeneration progresses beyond the early stages, vision becomes wavy and/or blurred. If macular degeneration continues to progress to advanced stages, central vision may be lost.

Although macular degeneration is currently considered to be incurable, treatments do exist that may slow the progression of the disease so as to prevent severe loss of vision. Treatment options include injection of an anti-angiogenic drug into the eye, laser therapy to destroy an actively growing abnormal blood vessel(s), and photodynamic laser therapy, which employs a light-sensitive drug to damage an abnormal blood vessel(s). Early detection of macular degeneration is of paramount importance in preventing advanced progression of macular degeneration prior to treatment to inhibit progression of the disease.

Early detection of macular degeneration can be accomplished using a suitable retinal imaging system. For example, Optical Coherence Tomography (OCT) is a non-invasive imaging technique relying on low coherence interferometry that can be used to generate a cross-sectional image of the macula. The cross-sectional view of the macula shows if the layers of the macula are distorted and can be used to monitor whether distortion of the layers of the macula has increased or decreased relative to an earlier cross-sectional image to assess the impact of treatment of the macular degeneration.

Existing OCT imaging systems, however, are typically expensive and may have to be operated by a trained technician. For example, a trained technician may be required to properly align an optical axis of the OCT imaging system with the optical axis of the eye examined. As a result, the use of such OCT imaging systems is typically restricted to specialized eye care clinics, thereby limiting use of such OCT imaging systems for widespread screening for early stage macular degeneration.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Ophthalmic imaging systems and related methods employ improved feedback to a user for use in self-alignment of the user's eye with the optical axis of the ophthalmic imaging system. In many embodiments, the user looks into a view port of the imaging device and is instructed to look at a fixation target, and perform a task. In some embodiments of the ophthalmic imaging systems and related methods disclosed herein, the user is shown two fiducials, one representing the optical axis of the device and the other one represents the center of the pupil and the task is to move "pupil" fiducial till the two are coincident. In some embodiments of the ophthalmic imaging systems and related methods disclosed herein, the fiducial representing the center of the pupil is displayed at a location that is, in many instances, offset by a controlled amount from where the fiducial would be displayed to indicate the actual position of the user's pupil relative to the optical axis of the imaging system. Showing an eye position fiducial at a location that is offset by a controlled amount from a location that would indicate the actual position of the user's pupil relative to the optical axis is in contrast to existing approaches. By displaying the eye position fiducial at a location that is offset by a controlled amount from a location at which the fiducial would be displayed to indicate the actual position of the user's pupil relative to the optical axis, the effort required by the user to achieve and maintain sufficient positioning of the user's pupil relative to the optical axis of the imaging device is reduced relative to prior approaches. For example, in some embodiments, the eye position fiducial is displayed coincident with optical axis fiducial when the actual position of the pupil is close enough to the optical axis to enable satisfactory imaging of the user's eye so as to avoid feedback to the user that may induce the user to try to reposition the user's eye when the current position of the user's eye is sufficiently close to the optical axis.

Thus, in one aspect, an ophthalmic imaging system includes an ophthalmic imaging device, a display device, an eye camera, and a control unit. The ophthalmic imaging device has an optical axis. The display device displays a fixation target viewable by an eye of a user. The eye camera is operable to image the eye to generate eye image data. The control unit processes the eye image data to determine a position of the eye relative to the optical axis. The control unit processes the position of the eye relative to the optical axis to generate a pseudo position of the eye relative to the optical axis. The pseudo position of the eye relative to the optical axis is different from the position of the eye relative to the optical axis. The control unit causes the display device to display an indication that provides feedback to the user that the eye is located at the pseudo position of the eye relative to the optical axis.

In many embodiments of the ophthalmic imaging system, the indication is displayed at a position relative to the fixation target. For example, the indication displayed to the user can include an eye pseudo position indicator displayed at a position relative to the fixation target matching the pseudo position of the eye relative to the optical axis. In many embodiments, if a distance between the position of the eye and the optical axis is less than an acceptable distance, the pseudo position of the eye relative to the optical axis is generated to lie on the optical axis. In many embodiments, the indication displayed to the user includes an eye pseudo position indicator displayed aligned with the fixation target to provide feedback to the user indicating that the position of the eye is located on the optical axis.

In some embodiments of the ophthalmic imaging system, the indication displayed to the user is based on a size of a pupil of the eye. In some embodiments, the acceptable distance is a function of the size of the pupil. For example, in some embodiments of the ophthalmic imaging system, the acceptable distance is smaller for a relatively small pupil and larger for a relatively large pupil. In some embodiments, the control unit processes the eye image data to determine the size of the pupil of the eye.

In some embodiments of the ophthalmic imaging system, the acceptable distance is increased in response to user achieving alignment of the eye of the user with the optical axis. For example, the acceptable distance can be set equal to a pre-alignment acceptable distance prior to the position of the eye being repositioned from being greater than the pre-alignment acceptable distance from the optical axis to being equal to or less than the pre-alignment acceptable distance from the optical axis. The acceptable distance can then be reset to a post-alignment acceptable distance in response to the position of the eye being repositioned from being greater than the pre-alignment acceptable distance from the optical axis to being equal to or less than the pre-alignment acceptable distance from the optical axis, the post-alignment acceptable distance being greater than the pre-alignment acceptable distance.

In some embodiments of the ophthalmic imaging system, the pre-alignment acceptable distance is based on a size of a pupil of the eye and/or the post-alignment acceptable distance is based on a size of a pupil of the eye. In some embodiments of the ophthalmic imaging system, the control unit processes the eye image data to determine the size of the pupil of the eye.

In some embodiments of the ophthalmic imaging system, the control unit is configured to detect the position of the eye even if a portion of a pupil of the eye is obscured. For example, in some embodiments, the control unit is configured to process the eye image data to (a) detect if a portion of the pupil of the eye is obscured, (b) identify an unobscured portion of the pupil, and (c) determine the position of the eye relative to the optical axis based on the unobscured portion of the pupil.

In many embodiments of the ophthalmic imaging system, the position of the eye relative to the optical axis is repeatedly determined to track the position of the eye relative to the optical axis. For example, in many embodiments the eye camera captures a series of images of the eye and the eye image data includes image data for each of the series of images of the eyes. In many embodiments, for each image of the series of images of the eye, the control unit (a) processes the eye image data to determine a respective position of the eye relative to the optical axis, (b) processes the respective position of the eye relative to the optical axis to generate a respective pseudo position of the eye relative to the optical axis, and (c) causes the display device to display a respective indication that provides feedback to the user that the eye is located at the respective pseudo position of the eye relative to the optical axis. In many embodiments, the respective pseudo position of the eye relative to the optical axis is different from the respective position of the eye relative to the optical axis. In many embodiments, the control unit processes, for the series of images of the eye, a series of positions of the eye relative to the optical axis to detect if the user fails to achieve and/or maintain acceptable positioning of the eye relative to the optical axis. In many embodiments, the control unit, in response to detecting failure of the user to achieve and/or maintain acceptable positioning of the eye relative to the optical axis, increases a size of the fixation target and/or the indication displayed to the user that provides the feedback to the user.

In many embodiments of the ophthalmic imaging system, the pseudo position of the eye is generated as a function of the position of the eye relative to the optical axis. For example, in some embodiments the controller includes a proportional controller and generation of the pseudo position of the eye relative to the optical axis by the control unit comprises multiplying, by the proportional controller, the position of the eye relative to the optical axis by a gain factor not equal to 1.0.

In many embodiments, if a distance of the eye relative to the optical axis is less than an acceptable distance, the pseudo position of the eye relative to the optical axis is generated to lie on the optical axis. In many embodiments, the indication displayed to the user includes an eye pseudo position indicator displayed aligned with the fixation target to provide feedback to the user indicating that the eye is located on the optical axis. For example, if the eye and the optical axis are not perfectly aligned but the offset between the optical axis and the pupil is small enough such that an imaging beam of the ophthalmic imaging device enters the pupil without any clipping, the user can be provided feedback that the user's eye is actually aligned with the optical axis so as to induce the user to hold still and avoid frustrating the user via providing feedback to the user suggesting that repositioning by the user is required when no repositioning by the user is actually required. The size of the acceptable offset between the actual position of the user's eye and the optical axis can be dependent on the beam diameter of the ophthalmic imaging device projected to the eye and the pupil diameter. For example, the acceptable offset can be provided by equation (1).

$$\text{Acceptable Offset} = ((\text{Pupil Diameter} - \text{Beam Diameter})/2) \qquad \text{Equation (1)}$$

In some embodiments, the acceptable offset may vary from 0.1 mm for a combination of a large beam (2.5 mm) and a small pupil diameter (2.7 mm) to 5.0 mm for a combination of a small beam (0.5 mm) and a large pupil (10.5 mm).

In another aspect, a method of providing feedback to a user of an ophthalmic imaging system regarding alignment of an eye of the user with an optical axis of the ophthalmic imaging system is described. The method includes displaying a fixation target on a display device viewable by the eye of the user. Eye image data corresponding to an image of the eye viewing the fixation target is generated by an eye camera. A control unit processes the eye image data to determine a position of the eye relative to the optical axis. The control unit generates a pseudo position of the eye relative to the optical axis based on the position of the eye relative to the optical axis. The pseudo position of the eye relative to the optical axis is generated to be different from the position of the eye relative to the optical axis. The control unit causes display of an indication on the display device to provide feedback to the user indicating that the eye is located at the pseudo position of the eye relative to the optical axis.

In many embodiments of the method, the indication is displayed at a position relative to the fixation target. For example, display of the indication on the display device can include display of a pseudo position indicator at a position relative to the fixation target matching the pseudo position of the eye relative to the optical axis. In many embodiments, the method further includes processing the position of the eye relative to the optical axis to determine if a distance between the position of the eye and the optical axis is less than acceptable distance. In many embodiments of the method, the generation of the pseudo position of the eye relative to the optical axis includes setting the pseudo position of the eye to lie on the optical axis if the distance of the eye relative to the optical axis is less than the acceptable distance. In many embodiments of the method, the display of the indication on the display device includes displaying an eye pseudo position indicator aligned with the fixation target to provide feedback to the user that the position of the eye is located on the optical axis.

In some embodiments, the method further includes determining the acceptable distance based on a size of a pupil of the eye. For example, in some embodiments of the method, the acceptable distance is smaller for a relatively small pupil and larger for a relatively large pupil. In some embodiments, the method further includes processing the eye image data, by the control unit, to determine the size of the pupil of the eye.

In some embodiments of the method, the acceptable distance is increased in response to user achieving alignment of the eye of the user with the optical axis. For example, the acceptable distance can be set equal to a pre-alignment acceptable distance prior to the position of the eye being repositioned from being greater than the pre-alignment acceptable distance from the optical axis to being equal to or less than the pre-alignment acceptable distance from the optical axis. The acceptable distance can then be reset to a post-alignment acceptable distance in response to the position of the eye being repositioned from being greater than the pre-alignment acceptable distance from the optical axis to being equal to or less than the pre-alignment acceptable distance from the optical axis, the post-alignment acceptable distance being greater than the pre-alignment acceptable distance.

In some embodiments, the method further includes determining the pre-alignment acceptable distance and/or the post-alignment acceptable distance based on a size of a pupil of the eye. In some embodiments, the method further includes processing the eye image data, by the control unit, to determine the size of the pupil of the eye.

In some embodiments of the method, the control unit is configured to detect the position of the eye even if a portion of the pupil is obscured. For example, in some embodiments, the method further includes processing the eye image data, by the controller, to (a) detect if a portion of a pupil of the eye is obscured, (b) identify an unobscured portion of the pupil, and (c) determine the position of the eye relative to the optical axis based on the unobscured portion of the pupil.

In many embodiments of the method, the position of the eye relative to the optical axis is repeatedly determined to track the position of the eye relative to the optical axis. For example, in many embodiments, the method includes generating, by the eye camera, the eye image data so as to comprise image data for each of a series of images of the eyes. In many embodiments, the method includes, for each image of the series of images of the eye, (a) processing the eye image data, by the control unit, to determine a respective position of the eye relative to the optical axis, (b) processing the respective position of the eye relative to the optical axis, by the control unit, to generate a respective pseudo position of the eye relative to the optical axis, the respective pseudo position of the eye relative to the optical axis being different from the respective position of the eye relative to the optical axis, and (c) causing, by the control unit, the display device to display a respective indication that provides feedback to the user that the eye is located at the respective pseudo position of the eye relative to the optical axis. In many embodiments, the method includes processing, by the control unit, for the series of images of the eye, a series of positions of the eye relative to the optical axis to detect if the user fails to achieve and/or maintain acceptable positioning of the eye relative to the optical axis. In many embodiments, the method includes, in response to detecting, by the control unit, failure of the user to achieve and/or maintain acceptable positioning of the eye relative to the optical axis, increasing, by the control unit, a size of the fixation target and/or the indication displayed to the user that provides the feedback to the user.

In many embodiments of the method, the pseudo position of the eye is generated as a function of the position of the eye relative to the optical axis. For example, generating the pseudo position of the eye relative to the optical axis can include multiplying the position of the eye relative to the optical axis by a factor not equal to 1.0. If a distance of the eye relative to the optical axis is less than an acceptable distance, the pseudo position of the eye relative to the optical axis can be generated to lie on the optical axis. The indication displayed to the user can include an eye pseudo position indicator displayed aligned with the fixation target to provide feedback to the user that the eye is located on the optical axis.

In another aspect, an ophthalmic imaging system includes an ophthalmic imaging device, a display device, an eye camera, and a control unit. The ophthalmic imaging device has an optical axis. The display device displays a fixation target viewable by an eye of a user. The eye camera is operable to image the eye to generate eye image data. The control unit processes the eye image data to determine a position of the eye relative to the optical axis. The control unit causes the display device to display an indication that provides feedback to the user that the eye is located at the position of the eye relative to the optical axis.

For a fuller understanding of the nature and advantages of the present invention, reference should be made to the ensuing detailed description and accompanying drawings.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Figure 1:
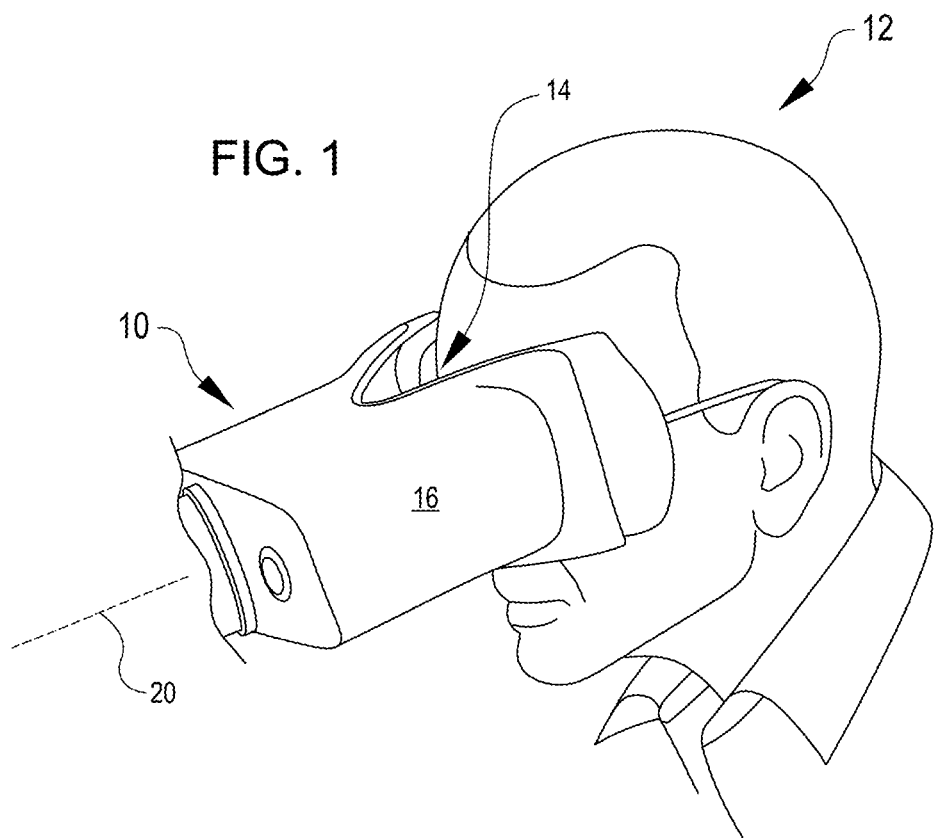
FIG. 1 shows a user looking into a view port of an ophthalmic imaging system, in accordance with some embodiments.

Referring now to the drawings, in which like reference numerals represent like parts throughout the several views, FIG. 1 shows a user 12 looking into a view port 14 of a viewing assembly 16 of an ophthalmic imaging system 10, in accordance with many embodiments. In many embodiments, the viewing assembly 16 is configured to approximately position one eye of the user 12 on an optical axis of the imaging system 10. For example, in the configuration shown in FIG. 1, the viewing assembly 16 is configured to approximately position the right eye of the user 12 on the optical axis of the imaging system 10. In the illustrated embodiment, the viewing assembly 16 can be rotated 180 degrees around a pivot axis 20 so as to reconfigure the viewing assembly 16 to approximately position the left eye of the user 12 on the optical axis of the imaging system 10. Accordingly, each of the right and the left eye of the user 12 can be selectively approximately positioned on the optical axis of the imaging system 10 for imaging of the respective eye by the imaging system 10. In embodiments described herein, final positioning and alignment of the optical axis of the respective eye of the user 12 with the optical axis of the imaging system 10 is accomplished by the user 12 adjusting the user's position relative to the view port 14 in response to feedback provided to the user 12 as described herein.

Figure 2:
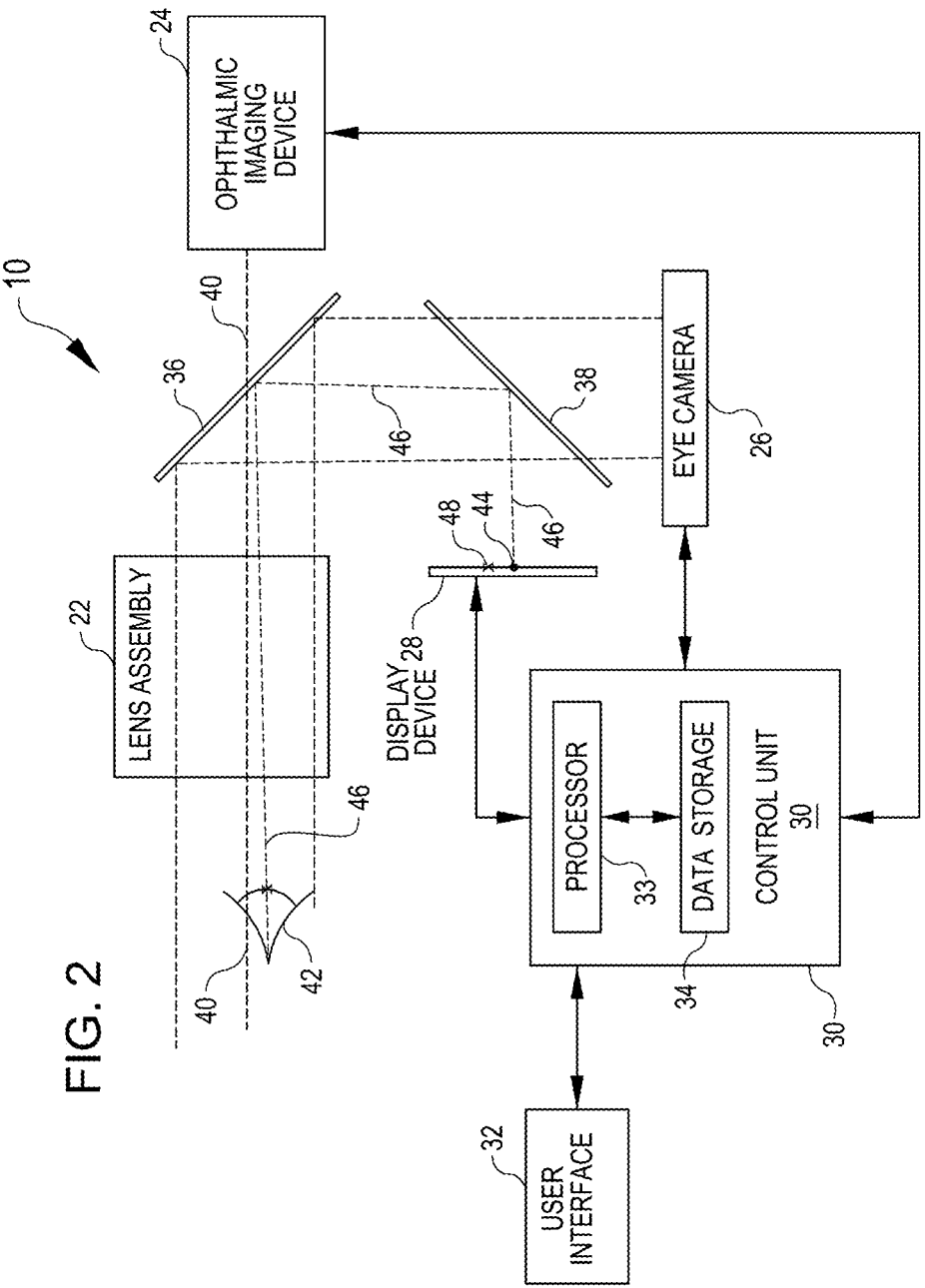
FIG. 2 is a simplified schematic illustration of an ophthalmic imaging system, in accordance with some embodiments.

FIG. 2 is a simplified schematic illustration of an embodiment of the ophthalmic imaging system 10. In the illustrated embodiment, the ophthalmic imaging system 10 includes a lens assembly 22, an ophthalmic imaging device 24, an eye camera 26, a display device 28, a control unit 30, a suitable user interface 32, a first beam splitter 36, and a second beam splitter 38. The ophthalmic imaging device 24 has an optical axis 40 to which the user 12 manually aligns a respective eye 42 of the user 12 in response to feedback provided to the user 12 described herein. The control unit 30 includes a processor 33 and a data storage device 34. A fixation target 44 is displayed on the display device 28 and is viewable by the eye 42 via an optical path 46 that extends through the lens assembly 22 and is diverted by each of the first beam splitter 36 and the second beam splitter 38. The display device 28, the first and second beam splitters 36, 38, and the position at which the fixation target 44 is displayed on the display device 28 are configured so that the portion of the optical path 46 between the eye 42 and the first beam splitter 36 aligns with the optical axis 40 of the imaging device 24 if the eye 42 is fixated on the fixation target 44 and the optical center of the eye 42 is positioned on the optical axis 40.

To generate the feedback to the user 12 to guide self-alignment of the optical center of the eye 42 with the optical axis 40 of the imaging device 24, the eye camera 26 images the eye 42 to generate eye image data corresponding to the captured image of the eye 42. The eye image data is transmitted from the eye camera 26 to the control unit 30. The control unit 30 processes the eye image data to detect the optical center of the eye 42 using any suitable approach. For example, in some embodiments, the control unit 30 processes the eye image data to detect the pupil of the eye 42 and then processes the region of the image of the eye corresponding to the detected pupil to locate the center of the pupil. The location of the detected center of the pupil can then be compared with a known fixed location of the optical axis 40 to determine the current relative position of the center of the eye 42 relative to the optical axis 40.

In many embodiments, the display device 28 projects a relatively large beam in the pupil plane (e.g., greater than 10 mm) in order to allow the user to see the projection at every pupil position and correct the pupil position accordingly. In many embodiments, the projection beam always contain the pupil inside in order to avoid a situation that the user cannot see the display or partially sees it.

Figure 3:
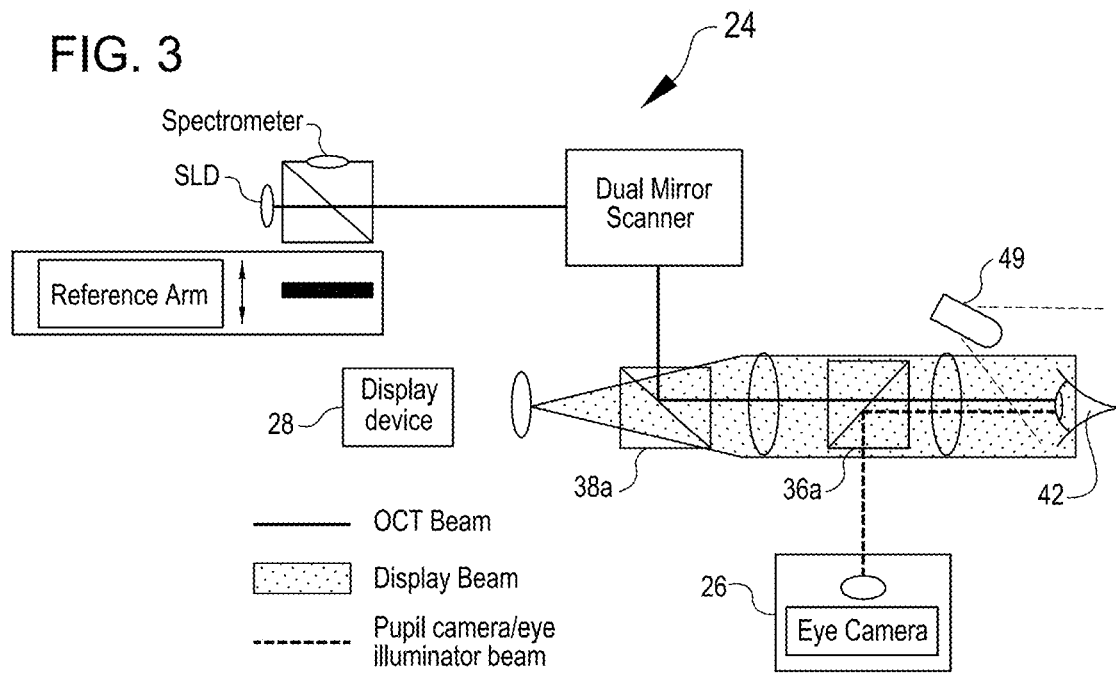
FIG. 3 is a simplified schematic illustration of another embodiment of optical components of the ophthalmic imaging system of FIG. 2.

It should be obvious to a person skilled in the art that any suitable optical assembly that includes the ophthalmic imaging device 24, the eye camera 26, and the display device 28 can be employed in the ophthalmic imaging system 10. For example, FIG. 3 is a simplified schematic illustration of such a suitable optical assembly that includes the ophthalmic imaging device 24, the eye camera 26, and the display device 28 and can be employed in the ophthalmic imaging system 10. In the illustrated optical assembly, the ophthalmic imaging device 24 is a spectral domain OCT imaging device that operates in a wavelength range of 800 nm to 900 nm. The illustrated optical assembly includes an eye illuminator 49 that illuminates the eye 42 using a suitable wavelength of light (e.g., a wavelength of light above 920 nm). In the illustrated optical assembly, the display device 28 can project light between any suitable wavelength (e.g., from 400 nm to 700 nm). The illustrated optical assembly includes a dichroic mirror 36a that transmits the OCT wavelength and the display wavelength range (400 nm to 900 nm) and reflects the illumination wavelength (e.g., greater than 920 nm) to the eye camera 26. The illustrated optical assembly includes a dichroic mirror 38a that transmits the display wavelength range and reflects the OCT wavelength.

In many embodiments, the control unit 30 generates a pseudo position of the eye 42 relative to the optical axis 40 as described herein with reference to FIG. 4 through FIG. 7 and displays an eye pseudo position indicator 48 on the display device 28 so as to provide feedback to the user 12 that the eye is located at the pseudo position of the eye relative to the optical axis 40. Any suitable approach can be used to provide the feedback to the user 12. For example, in many embodiments, the eye pseudo position indicator 48 is positioned on the display device 28 relative to the fixation target 44 by the pseudo position of the eye relative to the optical axis 40. In such embodiments, the fixation target 44 represents the location of the optical axis 40 and the position of the eye pseudo position indicator 48 relative to the fixation target 44 provides feedback to the user 12 indicating if the user 12 should reposition the user's eye relative to the view port 14, and if so, in what direction and by what distance.

In many embodiments, the control unit 30 is operatively coupled with, and controls operation of, the ophthalmic imaging device 24, the eye camera 26, and the display device 28. For example, in many embodiments, the control unit 30 receives the eye image data from the eye camera 26 and processes the eye image data to detect the location of the center of the eye 42 and determine the position of the center of the eye 42 relative to the optical axis 40. In many embodiments, the optical axis 40 is disposed at a fixed known position in an image of the eye captured by the eye camera 26 and the position of the center of the eye 42 within the image of the eye is compared with the position of the optical axis 40 within the image to determine the position of the center of the eye 42 relative to the optical axis 40. In some embodiments, the control unit 30 operates of the ophthalmic imaging device 24 when the center of the eye 42 is within an acceptable distance from the optical axis 40 and blocks operation of the ophthalmic imaging device 24 when the center of the eye 42 is not within an acceptable distance of the optical axis 40.

Figure 4:
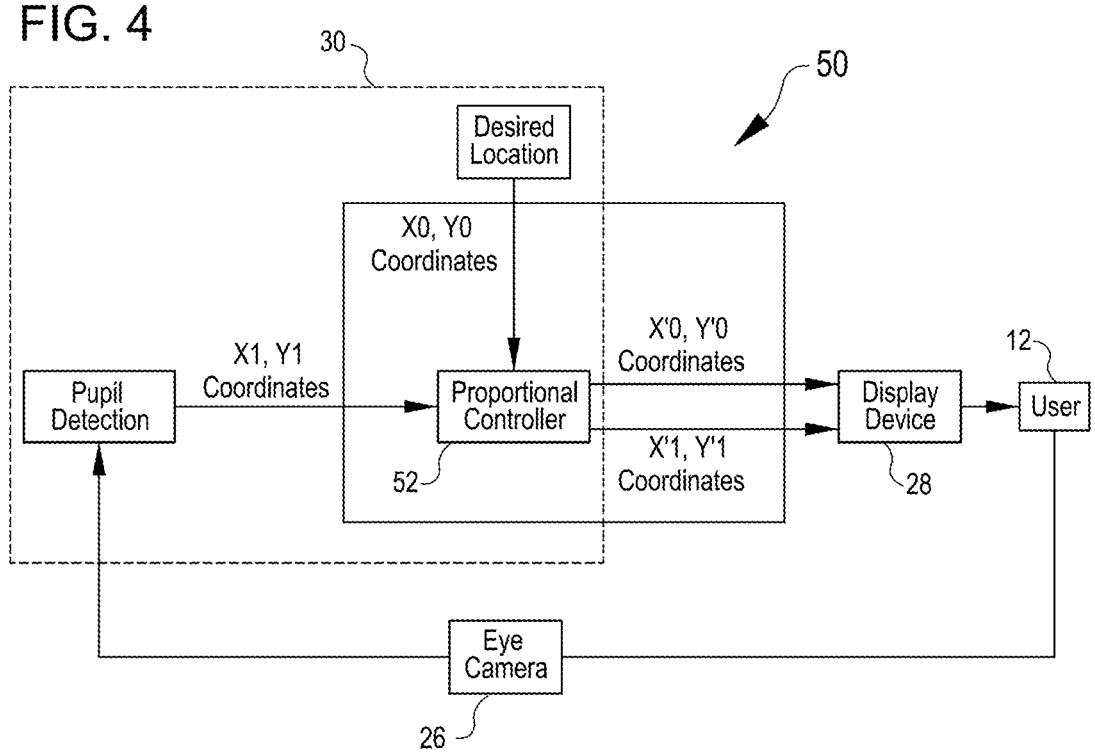
FIG. 4 is a simplified schematic illustration of a feedback loop that provides feedback to a user of an ophthalmic imaging system regarding alignment of the user's eye with an optical axis of the ophthalmic imaging system, in accordance with some embodiments.

In many embodiments, the control unit 30 is part of a feedback loop that provides the feedback to the user 12 as described herein. For example, FIG. 4 is a simplified schematic illustration of an example feedback loop 50 that provides the feedback described herein to the user 12 of the ophthalmic imaging device 24 regarding alignment of the user's eye 42 with the optical axis 40 of the ophthalmic imaging system 10. In many embodiments, the display device 28 displays an indication that is, in many instances, offset from the actual position of the user's eye 42 relative to the optical axis 40 by a controlled amount. By displaying an indication that is offset from the actual relative position of the user's eye 42 by the controlled amount, the effort required by the user 12 to achieve and maintain sufficient positioning of the user's eye 42 relative to the optical axis 40 of the ophthalmic imaging device 24 may be reduced relative to prior approaches.

Figure 5:
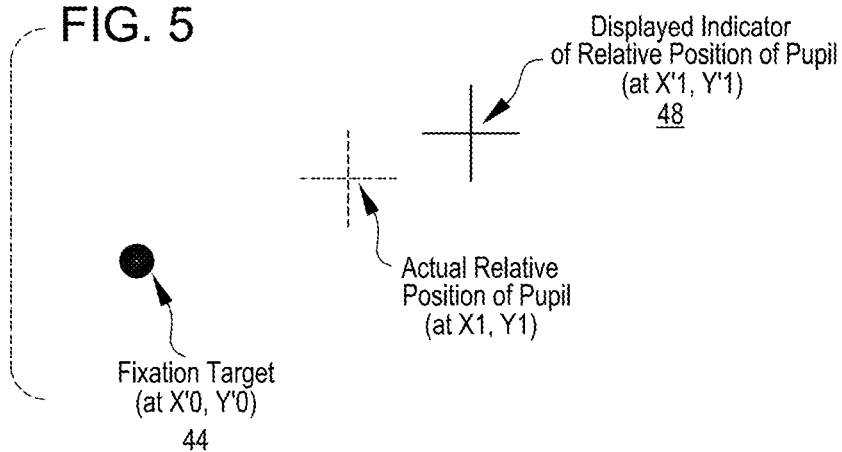
FIG. 5 illustrates display of an eye pseudo position indicator relative to a fixation target, in accordance with some embodiments.

In the illustrated embodiment of the feedback loop 50, the control unit 30 includes a proportional controller 52 that generates a pseudo position of the eye 42 (X'1, Y'1) from an actual position of the eye 42 (X1, Y1) and the position of the optical axis 40 (X0, Y0). The control unit 30 processes the eye image data from the eye camera 26 to determine the actual position of the eye 42 (X1, Y1). In some embodiments, the proportional controller 52 multiplies differences between actual position of the eye 42 (X1, Y1) and the position of the optical axis 40 (X0, Y0) by a predefined factor, referred to below as gain factor (G). For example, in some embodiments: (a) (X'1, Y'1) are the coordinates sent to the display device 28 from the proportional controller 52 at which the eye pseudo position indicator 48 is displayed to the user 12, (b) (X'0, Y'0)=(X0, Y0) (correspond to the location of the optical axis 40 of the imaging device 24 and the fixation target 44 displayed to the user 12), (c) (X1, Y1) are the coordinates of the actual position of the center of the eye 42 relative to the optical axis 40 of the imaging device 24, (d) X'1=X0+(X1−X0)*G is the x-coordinate of the eye pseudo position indicator 48 displayed to the user 12 on the display device 28, and (e) Y'1=Y0+(Y1−Y0)*G is the y-coordinate of the eye pseudo position indicator 48 displayed to the user 12 on the display device 28. An example display for a G=1.5 is shown in FIG. 5.

Figure 6:
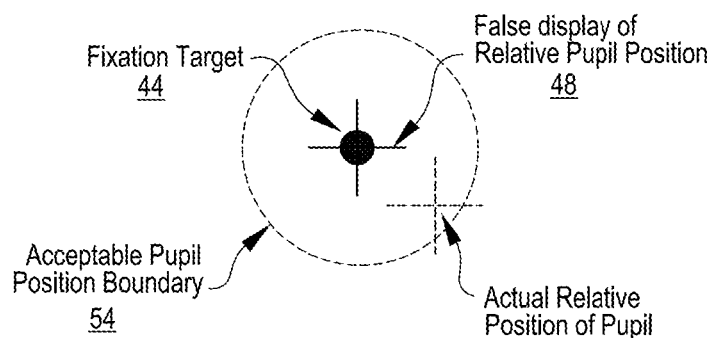
FIG. 6 illustrates display of an eye pseudo position indicator co-located with a fixation target, in accordance with some embodiments.

In many embodiments, if the eye 42 is not exactly positioned on the optical axis 40 of the ophthalmic imaging device 24, but is none-the-less positioned within an acceptable distance from the optical axis 40, the eye pseudo position indicator 48 is displayed on the display device 28 so as to give a false feedback to the user 12 that the eye 42 is centered on the optical axis 40. For example, as shown in FIG. 6, when the actual relative position of the pupil is within an acceptable pupil position boundary 54 (not actually displayed to the user in many embodiments), the eye pseudo position indicator 48 is displayed on the display device 28 aligned with the fixation target 44, thereby serving to inhibit the user 12 from further repositioning of the user's eye 42 relative to the view port 14. In many embodiments, the displayed location of the eye position pseudo indicator 48 changes suddenly when the position of the eye 42 is repositioned from outside of the acceptable pupil position boundary 54 to within the boundary 54, thereby appearing to the user 12 to snap between the displayed positions.

For example, in some embodiments the control unit 30 is configured to check if the current position of the eye 42 is within the acceptable pupil position boundary 54 relative to the optical axis 40 of the ophthalmic imaging device 24. If the current position of the eye 42 is within the acceptable pupil position boundary 54, then the control unit 30 sets X'1=X'0 and Y'1=Y'0 so that the eye pseudo position indicator 48 is placed on the fixation target 44. In other words, when the eye 42 is within a distance D of the optical axis 40 of the ophthalmic imaging device 24 (i.e., ((X1−X0)^2+(Y1−Y0)^2)^0.5<=D), then X'1=X'0 and Y'1=Y'0.

In some embodiments, the size of the acceptable pupil position boundary 54 is a function of the size of the pupil of the eye 42. For example, in some embodiments, the acceptable pupil position boundary is smaller for a relatively small pupil and larger for a relatively large pupil. In some embodiments, the size of the acceptable pupil position boundary 54 can be based in imaging requirements, which can be changed from one user to another, from one test to another, and/or from one disease state to another.

In some embodiments, the ophthalmic imaging system 10 is configured to detect when the user 12 is having trouble achieving and/or maintaining acceptable positioning of the user's eye 42 relative to the optical axis 40 of the ophthalmic imaging device 24. In response to detecting the user 12 having difficulty achieving and/or maintaining acceptable positioning of the user's eye 42 relative to the optical axis 40, the feedback provided to the user 12 via the display device can be modified to further assist the user 12. For example, the size of the fixation target 44 can be increased and/or the size of the eye pseudo position indicator 48 can be increased, which may further assist a user that has poor vision. Any suitable approach can be used to detect when the user 12 is having trouble achieving and/or maintaining acceptable positioning of the user's eye 42 relative to the optical axis 40. For example, if the user 12 fails to achieve acceptable positioning of the user's eye 42 relative to the optical axis 40 within a suitable time period and/or fails to maintain the eye 42 within the acceptable pupil position boundary 54 for a suitable time period, the system 10 can make a determination that the user 12 is having trouble positioning the eye 42 relative to the optical axis 40 and make suitable modifications to the feedback provided to the user 12, such as those modifications described herein, to aid the user's efforts.

In some embodiments, the control unit 30 is configured to detect the position of the eye 42 even if a portion of the pupil of the eye 42 is obscured (for example, when a drooped eye lid obscures a portion of the pupil). For example, in some embodiments, the control unit 30 processes the eye image data to detect if a portion of a pupil of the eye 42 is obscured. If a portion of the pupil of the eye 42 is obscured, the control unit 30 can identify an unobscured portion of the pupil, and determine the position of the eye 42 relative to the optical axis 40 based on the unobscured portion of the pupil.

In some embodiments, the control unit 30 is configured to display the actual position of the eye 42 relative to the optical axis 40. For example, the control unit 30 can be configured to cause the actual relative position of the pupil to be displayed at (X1, Y1) (see FIG. 4).

Figure 7:
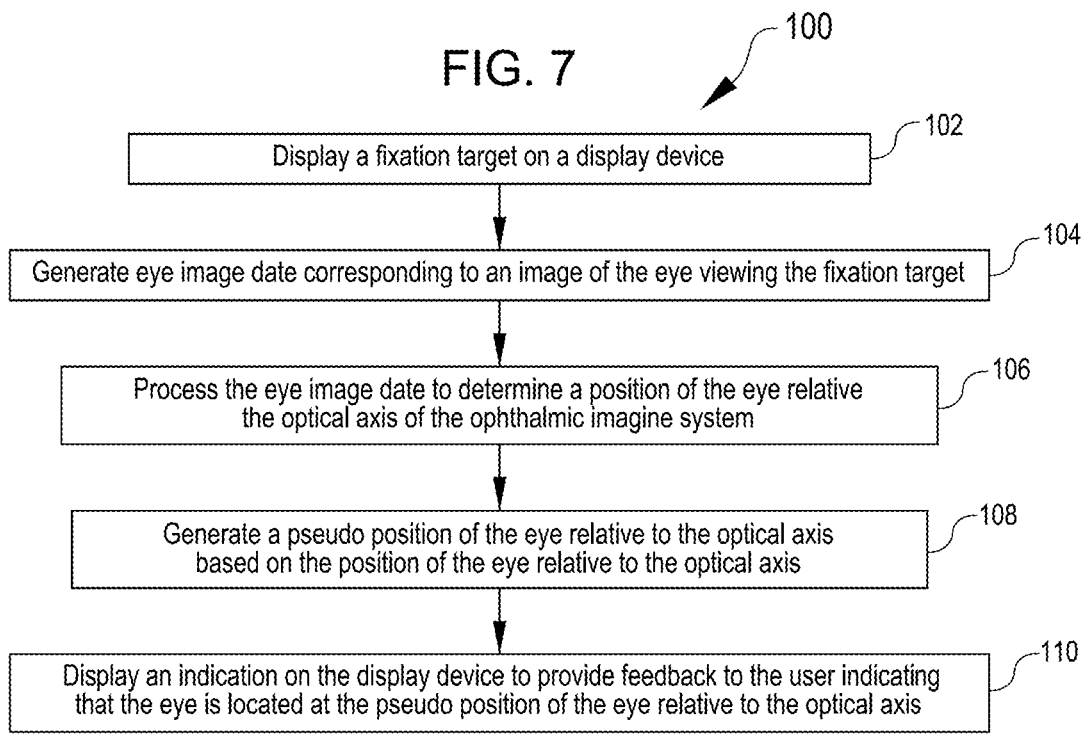
FIG. 7 is a simplified schematic block diagrams of acts of a method of providing feedback to a user of an ophthalmic imaging system regarding alignment of an eye of the user with an optical axis of the ophthalmic imaging system, in accordance with some embodiments.

FIG. 7 is a simplified schematic block diagrams of acts of a method 100 of providing feedback to a user of an ophthalmic imaging system regarding alignment of an eye of the user with an optical axis of the ophthalmic imaging system, in accordance with some embodiments. Any suitable ophthalmic imaging system, such as the ophthalmic imaging system 10 described herein, can be employed in the practice of the method 100. In the method 100, a fixation target is displayed to a user on a display device (act 102). Eye image data corresponding to an image of the eye viewing the fixation target is generated (act 104). The eye image data is processed to determine a position of the eye relative to the optical axis (act 106). A pseudo position of the eye relative to the optical axis is generated based on the position of the eye relative to the optical axis (act 108). An indication is displayed on the display device to provide feedback to the user indicating that the eye is located at the pseudo position of the eye relative to the optical axis (act 110).

Figure 8:
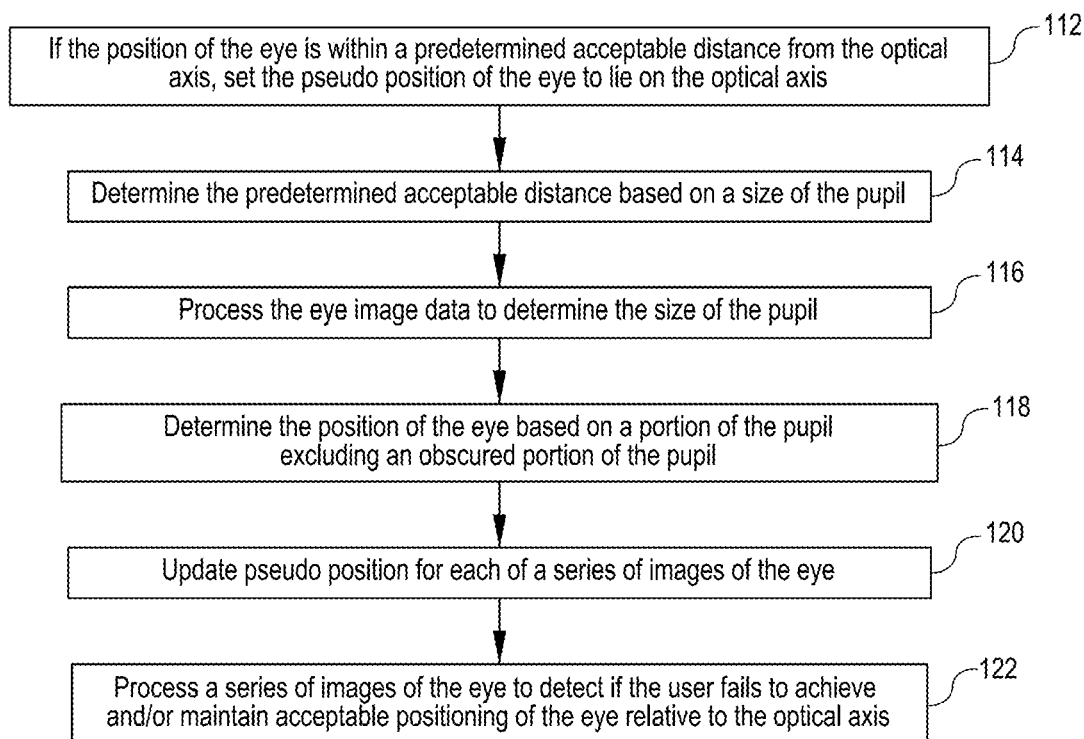
FIG. 8 is a simplified schematic block diagrams of additional acts that can be practiced in the method of FIG. 7, in accordance with some embodiments.

FIG. 8 is a simplified schematic block diagrams of additional acts that can be practiced in the method 100, in accordance with some embodiments. In act 112, if the position of the eye is within an acceptable distance from the optical axis, the pseudo position of the eye can be set to lie on the optical axis. In act 114, the acceptable distance is determined based on a size of the pupil of the user's eye. In act 116, the eye image data is processed to determine the size of the pupil of the user's eye. In act 118, the position of the eye is based on a portion of the pupil excluding an obscured portion of the pupil. In act 120, the pseudo position of the eye relative to the optical axis is repeatedly updated for each of a series of images of the eye. In act 122, a series of images of the eye is processed to detect if the user fails to achieve and/or maintain acceptable positioning of the eye relative to the optical axis.

Figure 9:
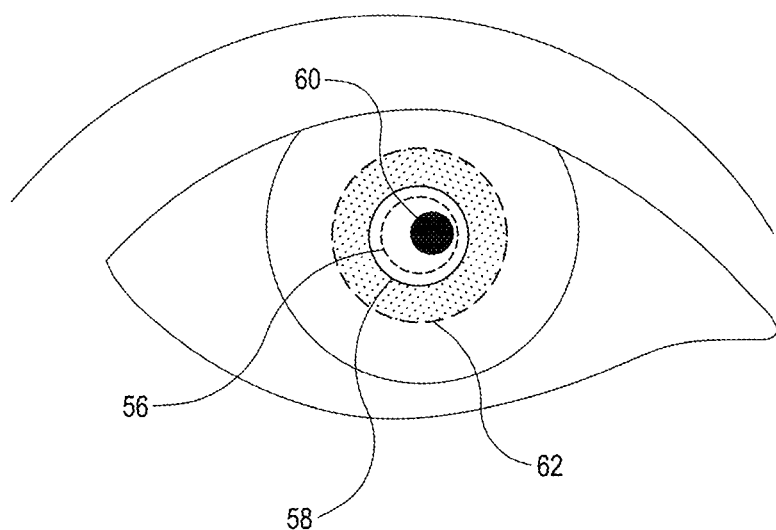
FIG. 9 illustrates pre-alignment and post-alignment acceptable alignment areas relative to an imaging area of the ophthalmic imaging system, in accordance with some embodiments.

In some embodiments of the ophthalmic imaging system 10, the acceptable distance is increased in response to user 12 achieving an initial acceptable alignment of the eye 42 with the optical axis 40. For example, FIG. 9 illustrates a pre-alignment acceptable alignment area 56 and a post-alignment acceptable alignment area 58 relative to an imaging area 60 of the ophthalmic imaging system 10. The acceptable distance is set equal to a pre-alignment acceptable distance (corresponding to the pre-alignment acceptable alignment area 56) prior to the position of the eye being repositioned from being greater than the pre-alignment acceptable distance from the optical axis 40 to being equal to or less than the pre-alignment acceptable distance from the optical axis 40. The acceptable distance is then reset to a post-alignment acceptable distance (corresponding to the post-alignment acceptable alignment area 58) in response to the position of the eye being repositioned from being greater than the pre-alignment acceptable distance from the optical axis 40 to being equal to or less than the pre-alignment acceptable distance from the optical axis 40. The post-alignment acceptable distance is greater than the pre-alignment acceptable distance. By allowing the user increased movement following achievement of the initial acceptable alignment of the user's eye 42 with the optical axis 40, the user is presented with decreased repositioning commands, and thereby experiences a more stable imaging session. The diameters of the pre-alignment acceptable alignment area 56 and the post-alignment acceptable area 58 can be based on the size of the pupil 62. For example, if the pupil 62 is relatively large, the diameters of the pre-alignment acceptable alignment area 56 and the post-alignment acceptable area 58 can be increased relative to those for smaller pupils so as to enable quicker alignment and improved experience for the user. Alternatively, the diameters of the pre-alignment acceptable alignment area 56 and the post-alignment acceptable area 58 can be based on size of the smallest pupil expected in a selected population of users.

Figure 10:
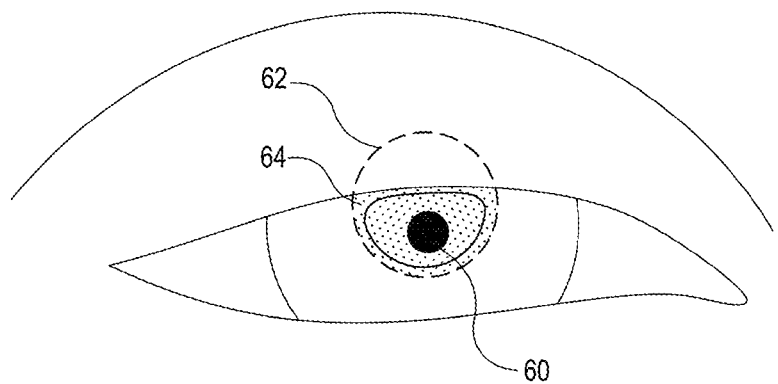
FIG. 10 illustrates an acceptable alignment area for a partially obscured pupil relative to an imaging area of the ophthalmic imaging system, in accordance with some embodiments.
Figure 11:
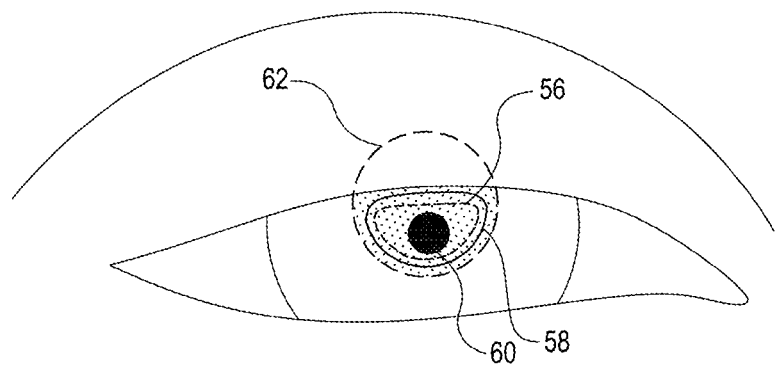
FIG. 11 illustrates pre-alignment and post-alignment acceptable alignment areas for a partially obscured pupil relative to an imaging area of the ophthalmic imaging system, in accordance with some embodiments.

In some embodiments of the ophthalmic imaging system 10, the control unit is configured to guide the user 12 to position the user's pupil based on an unobscured portion of the pupil instead of the center of the pupil. By guiding the user to position the user's pupil based on the unobscured portion of the pupil, blocking of the OCT imaging beam by the user's eyelid can be reduced. For example, FIG. 10 illustrates an acceptable alignment area 64 for a partially obscured pupil relative to the imaging area 60 of the ophthalmic imaging system 10. The acceptable alignment area 64 is shaped to overlay an unobstructed portion of a partially obscured pupil relative to the imaging area 60 of the ophthalmic imaging system 10. In many existing ophthalmic imaging systems, a pupil detection algorithm is employed that processes an image of the eye to identify the pupil by searching for a black circle or almost black circle feature in the image of the eye; the imaging beam is then aligned with the center of the pupil. The use of such an existing approach with an elderly user having a droopy eyelid, however, can result in a significant percentage of the light beam being blocked by the user's eyelid and the resulting OCT signal may be very weak or nonexistent. By shaping the acceptable alignment area 64 to overlay an unobstructed portion of a partially obscured pupil relative to the imaging area 60, the user 12 is provided feedback to align the imaging area 60 with the unobstructed portion of the user's pupil, thereby avoiding blockage of the OCT imaging beam via the user's eyelid. As another example, FIG. 11 illustrates that the pre-alignment acceptable alignment area 56 and the post-alignment acceptable alignment area 58 can be shaped to overlay an unobstructed portion of a partially obscured pupil.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

Examples of the embodiments of the present disclosure can be described in view of the following clauses:

Clause 1. An ophthalmic imaging system, comprising an ophthalmic imaging device having an optical axis, a display device displaying a fixation target viewable by an eye of a user, an eye camera operable to image the eye to generate eye image data, and a control unit. The control unit processes the eye image data to determine a position of the eye relative to the optical axis. The control unit processes the position of the eye relative to the optical axis to generate a pseudo position of the eye relative to the optical axis. The pseudo position of the eye relative to the optical axis is different from the position of the eye relative to the optical axis. The control unit causes the display device to display an indication that provides feedback to the user that the eye is located at the pseudo position of the eye relative to the optical axis.

Clause 2. The ophthalmic imaging system of clause 1, comprising a view port that is coupled to the ophthalmic imaging device.

Clause 3. The ophthalmic imaging system of any preceding clause, wherein the indication displayed to the user comprises an eye pseudo position indicator displayed at a position relative to the fixation target matching the pseudo position of the eye relative to the optical axis.

Clause 4. The ophthalmic imaging system of any preceding clause, wherein, if a distance between the position of the eye and the optical axis is less than an acceptable distance, the pseudo position of the eye relative to the optical axis is generated to lie on the optical axis.

Clause 5. The ophthalmic imaging system of clause 4, wherein the indication displayed to the user comprises an eye pseudo position indicator displayed aligned with the fixation target to provide feedback to the user indicating that the position of the eye is located on the optical axis.

Clause 6. The ophthalmic imaging system of clause 4, wherein the acceptable distance is based on a size of a pupil of the eye.

Clause 7. The ophthalmic imaging system of clause 6, wherein the control unit processes the eye image data to determine the size of the pupil of the eye.

Clause 8. The ophthalmic imaging system of clause 4, wherein the acceptable distance is equal to a pre-alignment acceptable distance prior to the position of the eye being repositioned from being greater than the pre-alignment acceptable distance from the optical axis to being equal to or less than the pre-alignment acceptable distance from the optical axis, and the acceptable distance is set to a post-alignment acceptable distance in response to the position of the eye being repositioned from being greater than the pre-alignment acceptable distance from the optical axis to being equal to or less than the pre-alignment acceptable distance from the optical axis, the post-alignment acceptable distance being greater than the pre-alignment acceptable distance.

Clause 9. The ophthalmic imaging system of clause 8, wherein the pre-alignment acceptable distance is based on a size of a pupil of the eye and/or the post-alignment acceptable distance is based on a size of a pupil of the eye.

Clause 10. The ophthalmic imaging system of clause 9, wherein the control unit processes the eye image data to determine the size of the pupil of the eye.

Clause 11. The ophthalmic imaging system of any preceding clause, wherein the control unit is configured to process the eye image data to detect if a portion of a pupil of the eye is obscured, identify an unobscured portion of the pupil, and determine the position of the eye relative to the optical axis based on the unobscured portion of the pupil.

Clause 12. The ophthalmic imaging system of clause 11, wherein if a distance between the position of the eye and to the optical axis is less than an acceptable distance, the pseudo position of the eye relative to the optical axis is generated to lie on the optical axis.

Clause 13. The ophthalmic imaging system of clause 12, wherein the acceptable distance is equal to a pre-alignment acceptable distance prior to the position of the eye being repositioned from being greater than the pre-alignment acceptable distance from the optical axis to being equal to or less than the pre-alignment acceptable distance from the optical axis, and the acceptable distance is set to a post-alignment acceptable distance in response to the position of the eye being repositioned from being greater than the pre-alignment acceptable distance from the optical axis to being equal to or less than the pre-alignment acceptable distance from the optical axis, the post-alignment acceptable distance being greater than the pre-alignment acceptable distance.

Clause 14. The ophthalmic imaging system of clause 13, wherein the pre-alignment acceptable distance is based on a size of a pupil of the eye and/or the post-alignment acceptable distance is based on a size of a pupil of the eye.

Clause 15. The ophthalmic imaging system of clause 14, wherein the control unit processes the eye image data to determine the size of the pupil of the eye.

Clause 16. The ophthalmic imaging system of any preceding clause, wherein the eye camera captures a series of images of the eye, and the eye image data comprises image data for each of the series of images of the eyes. For each image of the series of images of the eye, the control unit processes the eye image data to determine a respective position of the eye relative to the optical axis, and processes the respective position of the eye relative to the optical axis to generate a respective pseudo position of the eye relative to the optical axis. The respective pseudo position of the eye relative to the optical axis being different from the respective position of the eye relative to the optical axis. For each image of the series of images, the control unit causes the display device to display a respective indication that provides feedback to the user that the eye is located at the respective pseudo position of the eye relative to the optical axis.

Clause 17. The ophthalmic imaging system of clause 16, wherein the control unit processes, for the series of images of the eye, a series of positions of the eye relative to the optical axis to detect if the user fails to achieve and/or maintain acceptable positioning of the eye relative to the optical axis. The control unit, in response to detecting failure of the user to achieve and/or maintain acceptable positioning of the eye relative to the optical axis, increases a size of the fixation target and/or the indication displayed to the user that provides the feedback to the user.

Clause 18. The ophthalmic imaging system of any preceding clause, wherein the control unit comprises a proportional controller, and generation of the pseudo position of the eye relative to the optical axis by the control unit comprises multiplying, by the proportional controller, the position of the eye relative to the optical axis by a gain factor not equal to 1.0.

Clause 19. The ophthalmic imaging system of clause 18, wherein, if a distance between the position of the eye and the optical axis is less than an acceptable distance, the pseudo position of the eye relative to the optical axis is generated to lie on the optical axis.

Clause 20. The ophthalmic imaging system of clause 19, wherein the indication displayed to the user comprises an eye pseudo position indicator displayed aligned with the fixation target to provide feedback to the user indicating that the eye is located on the optical axis.

Clause 21. The ophthalmic imaging system of clause 19, wherein the acceptable distance is equal to a pre-alignment acceptable distance prior to the position of the eye being repositioned from being greater than the pre-alignment acceptable distance from the optical axis to being equal to or less than the pre-alignment acceptable distance from the optical axis, and the acceptable distance is set to a post-alignment acceptable distance in response to the position of the eye being repositioned from being greater than the pre-alignment acceptable distance from the optical axis to being equal to or less than the pre-alignment acceptable distance from the optical axis, the post-alignment acceptable distance being greater than the pre-alignment acceptable distance.

Clause 22. The ophthalmic imaging system of any preceding clause, wherein the ophthalmic imaging device comprises a spectral domain optical coherence tomography (OCT) imaging device that operates in a wavelength range of 800 nm to 900 nm, and the display device projects light in a wavelength range of 400 nm to 800 nm. The ophthalmic imaging system comprises an eye illuminator, a first dichroic mirror, and a second dichroic mirror. The eye illuminator illuminates the eye with light including a wavelength greater than 920 nm. The first dichroic mirror transmits light in a wavelength range of 400 nm to 900 nm and reflects light with a wavelength above 920 nm. The second dichroic mirror transmits light in a wavelength range between 400 nm to 800 nm and reflects light in a wavelength range between 800 nm and 900 nm.

Clause 23. The ophthalmic imaging system of any preceding clause, wherein the display device projects a beam in the plane of the pupil that extends beyond a 10 mm diameter circle.

Clause 24. A method of providing feedback to a user of an ophthalmic imaging system regarding alignment of an eye of the user with an optical axis of the ophthalmic imaging system. The method comprises displaying a fixation target on a display device viewable by the eye of the user; generating, by an eye camera, eye image data corresponding to an image of the eye viewing the fixation target; processing the eye image data, by a control unit, to determine a position of the eye relative to the optical axis; generating, by the control unit, a pseudo position of the eye relative to the optical axis based on the position of the eye relative to the optical axis, the pseudo position of the eye relative to the optical axis being different from the position of the eye relative to the optical axis; and causing, by the control unit, display of an indication on the display device to provide feedback to the user indicating that the eye is located at the pseudo position of the eye relative to the optical axis.

Clause 25. The method of clause 24, wherein display of the indication on the display device comprises display of an eye pseudo position indicator at a position relative to the fixation target matching the pseudo position of the eye relative to the optical axis.

Clause 26. The method of any of clause 24 and clause 25, further comprising processing the position of the eye relative to the optical axis to determine if a distance between the position of the eye and the optical axis is less than an acceptable distance, and wherein, if the distance between the position of the eye and the optical axis is less than the acceptable distance, the generation of the pseudo position of the eye relative to the optical axis comprises setting the pseudo position of the eye to lie on the optical axis.

Clause 27. The method of clause 26, wherein the display of the indication on the display device comprises displaying an eye pseudo position indicator aligned with the fixation target to provide feedback to the user that the eye is located on the optical axis.

Clause 28. The method of clause 27, further comprising determining the acceptable distance based on a size of a pupil of the eye.

Clause 29. The method of clause 28, further comprising processing the eye image data, by the control unit, to determine the size of the pupil of the eye.

Clause 30. The method of any of clause 26 through clause 29, wherein the acceptable distance is equal to a pre-alignment acceptable distance prior to the position of the eye being repositioned from being greater than the pre-alignment acceptable distance from the optical axis to being equal to or less than the pre-alignment acceptable distance from the optical axis, and the acceptable distance is set to a post-alignment acceptable distance in response to the position of the eye being repositioned from being greater than the pre-alignment acceptable distance from the optical axis to being equal to or less than the pre-alignment acceptable distance from the optical axis, the post-alignment acceptable distance being greater than the pre-alignment acceptable distance.

Clause 31. The method of clause 30, further comprising determining the pre-alignment acceptable distance and/or the post-alignment acceptable distance based on a size of a pupil of the eye.

Clause 32. The method of clause 31, further comprising processing the eye image data, by the control unit, to determine the size of the pupil of the eye.

Clause 33. The method of any of clause 24 through clause 32, further comprising processing the eye image data, by the controller, to detect if a portion of a pupil of the eye is obscured, identify an unobscured portion of the pupil, and determine the position of the eye relative to the optical axis based on the unobscured portion of the pupil.

Clause 34. The method of clause 33, wherein if a distance between the position of the eye and the optical axis is less than an acceptable distance, the pseudo position of the eye relative to the optical axis is generated to lie on the optical axis.

Clause 35. The method of clause 34, wherein the acceptable distance is equal to a pre-alignment acceptable distance prior to the position of the eye being repositioned from being greater than the pre-alignment acceptable distance from the optical axis to being equal to or less than the pre-alignment acceptable distance from the optical axis, and the acceptable distance is set to a post-alignment acceptable distance in response to the position of the eye being repositioned from being greater than the pre-alignment acceptable distance from the optical axis to being equal to or less than the pre-alignment acceptable distance from the optical axis, the post-alignment acceptable distance being greater than the pre-alignment acceptable distance.

Clause 36. The method of clause 35, further comprising determining the pre-alignment acceptable distance and/or the post-alignment acceptable distance based on a size of a pupil of the eye.

Clause 37. The method of clause 36, further comprising processing the eye image data, by the control unit, to determine the size of the pupil of the eye.

Clause 38. The method of any of clause 24 through clause 37, comprising generating, by the eye camera, the eye image data so as to comprise image data for each of a series of images of the eyes. The method further comprising, for each image of the series of images of the eye, processing the eye image data, by the control unit, to determine a respective position of the eye relative to the optical axis; processing the respective position of the eye relative to the optical axis, by the control unit, to generate a respective pseudo position of the eye relative to the optical axis, the respective pseudo position of the eye relative to the optical axis being different from the respective position of the eye relative to the optical axis; and causing, by the control unit, the display device to display a respective indication that provides feedback to the user that the eye is located at the respective pseudo position of the eye relative to the optical axis.

Clause 39. The method of clause 38, comprising processing, by the control unit, for the series of images of the eye, a series of positions of the eye relative to the optical axis to detect if the user fails to achieve and/or maintain acceptable positioning of the eye relative to the optical axis; and in response to detecting, by the control unit, failure of the user to achieve and/or maintain acceptable positioning of the eye relative to the optical axis, increasing, by the control unit, a size of the fixation target and/or the indication displayed to the user that provides the feedback to the user.

Clause 40. The method of any of clause 24 through clause 39, wherein the generation of the pseudo position of the eye relative to the optical axis comprises multiplying the position of the eye relative to the optical axis by a factor not equal to 1.0.

Clause 41. The method of clause 40, wherein, if a distance of the eye relative to the optical axis is less than an acceptable distance, the pseudo position of the eye relative to the optical axis is generated to lie on the optical axis.

Clause 42. The method of clause 41, wherein the indication displayed to the user comprises an eye pseudo position indicator displayed aligned with the fixation target to provide feedback to the user that the eye is located on the optical axis.

Clause 43. The method of any of clause 41 and clause 42, wherein the acceptable distance is equal to a pre-alignment acceptable distance prior to the position of the eye being repositioned from being greater than the pre-alignment acceptable distance from the optical axis to being equal to or less than the pre-alignment acceptable distance from the optical axis; and the acceptable distance is set to a post-alignment acceptable distance in response to the position of the eye being repositioned from being greater than the pre-alignment acceptable distance from the optical axis to being equal to or less than the pre-alignment acceptable distance from the optical axis, the post-alignment acceptable distance being greater than the pre-alignment acceptable distance.

Clause 44. An ophthalmic imaging system, comprimising an ophthalmic imaging device having an optical axis, a display device displaying a fixation target viewable by an eye of a user, an eye camera operable to image the eye to generate eye image data, and a control unit. The control unit processes the eye image data to determine a position of the eye relative to the optical axis, and causes the display device to display an indication that provides feedback to the user that the eye is located at the position of the eye relative to the optical axis.

What is claimed is:

1. An ophthalmic imaging system, comprising:
   an ophthalmic imaging device having an optical axis;
   a display device displaying a fixation target viewable by an eye of a user;
   an eye camera operable to image the eye to generate eye image data; and
   a control unit that:
      processes the eye image data to determine a position of the eye relative to the optical axis;
      processes the position of the eye relative to the optical axis to generate a pseudo position of the eye relative to the optical axis, the pseudo position of the eye relative to the optical axis being different from the position of the eye relative to the optical axis; and
      causes the display device to display an indication that provides feedback to the user that the eye is located at the pseudo position of the eye relative to the optical axis;
   wherein, if a distance between the position of the eye and the optical axis is less than an acceptable distance, the pseudo position of the eye relative to the optical axis is generated to lie on the optical axis;
   wherein the acceptable distance is equal to a pre-alignment acceptable distance prior to the position of the eye being repositioned from being greater than the pre-alignment acceptable distance from the optical axis to being equal to or less than the pre-alignment acceptable distance from the optical axis; and
   wherein the acceptable distance is set to a post-alignment acceptable distance in response to the position of the eye being repositioned from being greater than the pre-alignment acceptable distance from the optical axis to being equal to or less than the pre-alignment acceptable distance from the optical axis, the post-alignment acceptable distance being greater than the pre-alignment acceptable distance.

2. The ophthalmic imaging system of claim 1, comprising a view port that is coupled to the ophthalmic imaging device.

3. The ophthalmic imaging system of claim 1, wherein the indication displayed to the user comprises an eye pseudo position indicator displayed at a position relative to the fixation target matching the pseudo position of the eye relative to the optical axis.

4. The ophthalmic imaging system of claim 1, wherein the indication displayed to the user comprises an eye pseudo position indicator displayed aligned with the fixation target to provide feedback to the user indicating that the position of the eye is located on the optical axis.

5. The ophthalmic imaging system of claim 1, wherein the acceptable distance is based on a size of a pupil of the eye.

6. The ophthalmic imaging system of claim 1, wherein the pre-alignment acceptable distance is based on a size of a pupil of the eye and/or the post-alignment acceptable distance is based on a size of a pupil of the eye.

7. The ophthalmic imaging system of claim 1, wherein:
the eye camera captures a series of images of the eye;
the eye image data comprises image data for each of the series of images of the eyes; and
for each image of the series of images of the eye, the control unit:
processes the eye image data to determine a respective position of the eye relative to the optical axis;
processes the respective position of the eye relative to the optical axis to generate a respective pseudo position of the eye relative to the optical axis, the respective pseudo position of the eye relative to the optical axis being different from the respective position of the eye relative to the optical axis; and
causes the display device to display a respective indication that provides feedback to the user that the eye is located at the respective pseudo position of the eye relative to the optical axis.

8. The ophthalmic imaging system of claim 7, wherein:
the control unit processes, for the series of images of the eye, a series of positions of the eye relative to the optical axis to detect if the user fails to achieve and/or maintain acceptable positioning of the eye relative to the optical axis; and
the control unit, in response to detecting failure of the user to achieve and/or maintain acceptable positioning of the eye relative to the optical axis, increases a size of the fixation target and/or the indication displayed to the user that provides the feedback to the user.

9. The ophthalmic imaging system of claim 1, wherein:
the control unit comprises a proportional controller; and
generation of the pseudo position of the eye relative to the optical axis by the control unit comprises multiplying, by the proportional controller, the position of the eye relative to the optical axis by a gain factor not equal to 1.0.

10. The ophthalmic imaging system of claim 9, wherein, if a distance between the position of the eye and the optical axis is less than an acceptable distance, the pseudo position of the eye relative to the optical axis is generated to lie on the optical axis.

11. The ophthalmic imaging system of claim 10, wherein the indication displayed to the user comprises an eye pseudo position indicator displayed aligned with the fixation target to provide feedback to the user indicating that the eye is located on the optical axis.

12. The ophthalmic imaging system of claim 10, wherein:
the acceptable distance is equal to a pre-alignment acceptable distance prior to the position of the eye being repositioned from being greater than the pre-alignment acceptable distance from the optical axis to being equal to or less than the pre-alignment acceptable distance from the optical axis; and
the acceptable distance is set to a post-alignment acceptable distance in response to the position of the eye being repositioned from being greater than the pre-alignment acceptable distance from the optical axis to being equal to or less than the pre-alignment acceptable distance from the optical axis, the post-alignment acceptable distance being greater than the pre-alignment acceptable distance.

13. The ophthalmic imaging system of claim 1, wherein:
the ophthalmic imaging device comprises a spectral domain optical coherence tomography (OCT) imaging device that operates in a wavelength range of 800 nm to 900 nm;
the display device projects light in a wavelength range of 400 nm to 800 nm; and
the ophthalmic imaging system comprises an eye illuminator, a first dichroic mirror, and a second dichroic mirror, the eye illuminator illuminating the eye with light including a wavelength greater than 920 nm, the first dichroic mirror transmitting light in a wavelength range of 400 nm to 900 nm and reflecting light with a wavelength above 920 nm, the second dichroic mirror transmitting light in a wavelength range between 400 nm to 800 nm and reflecting light in a wavelength range between 800 nm and 900 nm.

14. An ophthalmic imaging system comprising:
an ophthalmic imaging device having an optical axis;
a display device displaying a fixation target viewable by an eye of a user;
an eye camera operable to image the eye to generate eye image data; and
a control unit that:
processes the eye image data to determine a position of the eye relative to the optical axis;
processes the position of the eye relative to the optical axis to generate a pseudo position of the eye relative to the optical axis, the pseudo position of the eye relative to the optical axis being different from the position of the eye relative to the optical axis; and
causes the display device to display an indication that provides feedback to the user that the eye is located at the pseudo position of the eye relative to the optical axis; and
wherein the control unit is configured to process the eye image data to:
detect if a portion of a pupil of the eye is obscured;
identify an unobscured portion of the pupil; and
determine the position of the eye relative to the optical axis based on the unobscured portion of the pupil.

15. The ophthalmic imaging system of claim 14, wherein if a distance between the position of the eye and to the optical axis is less than an acceptable distance, the pseudo position of the eye relative to the optical axis is generated to lie on the optical axis.

16. The ophthalmic imaging system of claim 15, wherein:
the acceptable distance is equal to a pre-alignment acceptable distance prior to the position of the eye being repositioned from being greater than the pre-alignment acceptable distance from the optical axis to being equal to or less than the pre-alignment acceptable distance from the optical axis; and the acceptable distance is set to a post-alignment acceptable distance in response to the position of the eye being repositioned from being greater than the pre-alignment acceptable distance from the optical axis to being equal to or less than the pre-alignment acceptable distance from the optical axis, the post-alignment acceptable distance being greater than the pre-alignment acceptable distance.

17. The ophthalmic imaging system of claim 15, wherein the indication displayed to the user comprises an eye pseudo position indicator displayed aligned with the fixation target to provide feedback to the user indicating that the position of the eye is located on the optical axis.

18. The ophthalmic imaging system of claim 15, wherein the acceptable distance is based on a size of a pupil of the eye.

19. The ophthalmic imaging system of claim 14, wherein the indication displayed to the user comprises an eye pseudo position indicator displayed at a position relative to the fixation target matching the pseudo position of the eye relative to the optical axis.

20. An ophthalmic imaging system comprising:
an ophthalmic imaging device having an optical axis;
a display device displaying a fixation target viewable by an eye of a user;
an eye camera operable to image the eye to generate eye image data; and
a control unit that:
processes the eye image data to determine a position of the eye relative to the optical axis;
processes the position of the eye relative to the optical axis to generate a pseudo position of the eye relative to the optical axis, the pseudo position of the eye relative to the optical axis being different from the position of the eye relative to the optical axis; and
causes the display device to display an indication that provides feedback to the user that the eye is located at the pseudo position of the eye relative to the optical axis; and
wherein the display device projects a beam that extends beyond a 10 mm diameter circle at a plane aligned with a pupil of the user's eye.

21. The ophthalmic imaging system of claim 20, wherein the indication displayed to the user comprises an eye pseudo position indicator displayed at a position relative to the fixation target matching the pseudo position of the eye relative to the optical axis.

22. The ophthalmic imaging system of claim 20, wherein, if a distance between the position of the eye and the optical axis is less than an acceptable distance, the pseudo position of the eye relative to the optical axis is generated to lie on the optical axis.

23. The ophthalmic imaging system of claim 22, wherein the indication displayed to the user comprises an eye pseudo position indicator displayed aligned with the fixation target to provide feedback to the user indicating that the position of the eye is located on the optical axis.

24. The ophthalmic imaging system of claim 22, wherein the acceptable distance is based on a size of a pupil of the eye.

* * * * *